United States Patent
Dreiner et al.

(10) Patent No.: US 9,412,501 B2
(45) Date of Patent: Aug. 9, 2016

(54) ARTICLE AND METHOD FOR PRODUCING AN ARTICLE WITH A SILICONE-TYPE BASE MATERIAL AND SOLID MATERIAL PARTICLES INTRODUCED INTO A SURFACE OF THE ARTICLE

(71) Applicant: LEONI KABEL HOLDING GMBH, Nuremberg (DE)

(72) Inventors: Michael Dreiner, Wipperfuerth (DE); Albert Nording, Boesel (DE)

(73) Assignee: Leoni Kabel Holding GmbH, Nuremberg (DE)

( * ) Notice: Subject to any disclaimer, the term of this patent is extended or adjusted under 35 U.S.C. 154(b) by 71 days.

(21) Appl. No.: 14/552,752

(22) Filed: Nov. 25, 2014

(65) Prior Publication Data
US 2015/0075841 A1    Mar. 19, 2015

Related U.S. Application Data

(63) Continuation of application No. PCT/EP2013/060807, filed on May 24, 2013.

(30) Foreign Application Priority Data

May 25, 2012  (DE) .......................... 10 2012 208 871

(51) Int. Cl.
*H01B 7/00*    (2006.01)
*H01B 13/14*   (2006.01)
*A61N 1/05*    (2006.01)
(Continued)

(52) U.S. Cl.
CPC .............. *H01B 13/14* (2013.01); *A61L 29/126* (2013.01); *A61L 29/14* (2013.01); *A61N 1/05* (2013.01); *C09D 183/04* (2013.01); *H01B 3/46* (2013.01); *H01B 7/292* (2013.01); *H01B 13/145* (2013.01); *A61L 2400/10* (2013.01); *B05D 2256/00* (2013.01); *B05D 2401/32* (2013.01); *H01B 13/0033* (2013.01)

(58) Field of Classification Search
USPC ...... 174/110 R–110 S, 112, 116, 118, 119 R, 174/120 R, 121 R, 121 AR, 112 R, 122 C, 174/120 AR
See application file for complete search history.

(56) References Cited

U.S. PATENT DOCUMENTS 2,421,652 A * 6/1947 Robinson ................ C25B 13/00
                                                174/110 A
2,593,922 A * 4/1952 Robinson ................ H01B 9/02
                                                174/110 R (Continued)

FOREIGN PATENT DOCUMENTS

CH            605127 A5    9/1978
EP            1691374 A *  6/2005  ............... H01B 3/46

(Continued)

*Primary Examiner* — William H Mayo, III
(74) *Attorney, Agent, or Firm* — Laurence A. Greenberg; Werner H. Stemer; Ralph E. Locher

(57) ABSTRACT

A silicone article, such as a cable with a silicone outer jacket. Solid mica particles are introduced into the surface of the cable or other article. An intermediate product which has a silicone-type base material on the exterior is initially provided in a state that is not, or no more than partially, cross-linked. The solid material particles are subsequently pressed in, before the complete cross-linking takes place. The solid material particles are present only in the surface region.

14 Claims, 3 Drawing Sheets

(51) Int. Cl.
*A61L 29/12* (2006.01)
*A61L 29/14* (2006.01)
*C09D 183/04* (2006.01)
*H01B 3/46* (2006.01)
*H01B 7/29* (2006.01)
*H01B 13/00* (2006.01)

(56) References Cited

U.S. PATENT DOCUMENTS

| | | | | |
|---|---|---|---|---|
| 2,953,466 A | * | 9/1960 | Brown | C04B 26/32 106/287.1 |
| 3,427,189 A | * | 2/1969 | Habib | H01B 3/002 156/53 |
| 5,650,193 A | | 7/1997 | Swain et al. | |
| 2010/0075018 A1 | | 3/2010 | Desai et al. | |
| 2012/0022624 A1 | | 1/2012 | Guenther et al. | |
| 2013/0240241 A1 | * | 9/2013 | Dubrow | H01B 3/004 174/113 R |

FOREIGN PATENT DOCUMENTS

| | | |
|---|---|---|
| EP | 1691374 B1 | 11/2009 |
| EP | 2409725 A1 | 1/2012 |
| JP | 2001035267 A | 2/2001 |

\* cited by examiner

ARTICLE AND METHOD FOR PRODUCING AN ARTICLE WITH A SILICONE-TYPE BASE MATERIAL AND SOLID MATERIAL PARTICLES INTRODUCED INTO A SURFACE OF THE ARTICLE

CROSS-REFERENCE TO RELATED APPLICATION

This application is a continuation, under 35 U.S.C. §120, of copending international application No. PCT/EP2013/060807, filed May 24, 2013, which designated the United States; this application also claims the priority, under 35 U.S.C. §119, of German patent application No. DE 10 2012 208 871.7, filed May 25, 2012; the prior applications are herewith incorporated by reference in their entirety.

BACKGROUND OF THE INVENTION

Field of the Invention

The invention relates to a method for producing an element, particularly a cable, which has on the outside a silicone-type base material. The invention relates, furthermore, to such an element.

The element is, in particular, an electrical cable with a cable sheath made from silicone. However, the invention is not restricted to the field of use of electrical cables.

Electrical cables with a silicone sheath are employed, for example in medical technology, because of their special properties. To be precise, on the one hand, silicone as the material is distinguished by very high flexibility or elasticity, so that highly flexible elastic cables, for example with diameters ranging from 1 mm to 10 mm, can thereby be formed. At the same time, silicone also has a high continuous use temperature of about 180° C. Such cables are therefore suitable for medical applications in which the cables regularly have to be sterilized. This takes place usually with the aid of so-called steam sterilization at temperatures of about 140° C. to 150° C.

An electrode line for medical use is described in U.S. patent application publication No. US 2012/0022624 A1 and its counterpart European published patent application EP 2 409 725 A1. There, electrical conductors are introduced into an insulating hose and therefore to some extent lie loosely in the hose. The electrode line serves for use inside the body, for example for heart pacemaker electrode lines. To improve the abrasion resistance of the hose, particulate filling material is introduced into the base material of the hose. The base material is, for example, silicone, polyurethane, polyamide, PTFE, etc. To produce the insulating hose, the filler particles are admixed to an extrudate and are then extruded or injected to form the insulating hose. In a design variant, a two-layer insulating hose is formed by coextrusion, and in this only the outer layer is filled with the filler material. Alternatively to extrusion, a basic hose is dipped into a low-viscosity base material which is mixed with the film material in order to form the outer layer.

On account of the good temperature resistance of silicone, silicone is also adopted, in particular, for fire-resistant cables. To improve the fire resistance, as described, for instance in Japanese patent application publication JP 2001035267 the introduction of filler materials, to be precise mica particles, is likewise provided.

SUMMARY OF THE INVENTION

It is accordingly an object of the invention to provide a method and an article of manufacture which overcome the above-mentioned and other disadvantages of the heretofore-known devices and methods of this general type and which provides for a novel method for producing an element, such as a cable, and also an element, particularly a cable, which is preferably produced by the novel method and which is suitable, in particular, for a medical use environment and, while being simple to produce, makes it possible to have improved properties, as compared with prior art cables.

With the foregoing and other objects in view there is provided, in accordance with the invention, a method of producing an article or manufacture, in particular an electrical cable, with an exterior surface of a silicone-type material, the method comprising:

in a first step, fashioning an at least partially non-cross-linked base material into an intermediate product;

subsequently, in a second step, introducing solid mica particles into the surface by guiding the at least partially non-cross-linked intermediate product through a reservoir containing the solid mica particles therein, and exposing the reservoir to vibration or generating in the reservoir a vortex or an airstream to thereby mechanically press the solid mica particles into the surface and to cause the particles to be distributed over the surface, with a dot-shaped contact zone formed in each case, and wherein at least some of the solid mica particles project out of the surface as scales; and subsequently, in a third step, cross-linking the at least partially non-cross-linked base material.

In other words, the objects of the invention are achieved by way of a method for producing an article, particularly a cable, which has on the outside a silicone-type base material. In a first step, the silicone-like base material is first fashioned into a non-cross-linked, at least not completely cross-linked intermediate product. Subsequently, in a second step, solid particles are introduced into the surface, and finally, in a third step, the non-cross-linked or only partially cross-linked base material is cross-linked up to the desired degree of cross-linking, in particular is cross-linked completely.

In this method, therefore, the at least partially non-cross-linked state of the base material is utilized in order to introduce the solid particles into the surface of the base material. On account of the non-cross-linked state, this is possible in a simple way in terms of the process employed. As a result of the subsequent cross-linking operation, the solid particles are then incorporated firmly into the surface. The solid particles are applied loosely as such and are therefore not embedded in a carrier material. The solid particles are in the form of a powder.

The solid particles are therefore introduced from outside solely into the surface. There is no incorporation of the solid particles as filler material into the volume of the base material. By virtue of the chosen production method, the depth of penetration of the solid particles is therefore also usually limited at most to the extent of the solid particles. The solid particles are therefore not admixed to the base material during the production process.

This method is based on the recognition that elements, in particular cables with an silicone-type outer material, i.e., a material that is at least silicone-like or is composed of silicone, have a high coefficient of friction. This often leads to a downright "adhesion" of the element to surfaces, such as, for example, to an operating table or even to the human skin.

Proceeding from this, the invention is based on the idea of beneficially influencing the silicone-specific feel by the introduction of solid particles solely on the surface and, in particular, of markedly reducing the coefficient of friction at the surface, in order to avoid or at least reduce undesirable adhesion. By the solid particles being applied merely on the surface, the solid particles regularly project somewhat above the surface formed by the base material. Friction is therefore determined critically by the solid particles. On account of their nature and structure in comparison with silicone, friction is markedly reduced. Furthermore, the loose distribution of the solid particles over the surface has an advantageous effect, so that there is no full surface friction, but instead only a punctiform contact zone occurs in each case.

The terms silicone-type or silicone-like base material is understood in general to mean cross-linkable plastics which in the final cross-linked state have, in particular, a coefficient of friction comparable to silicone. Other such base materials in addition to silicones themselves are also polyurethanes, polyamides, polytetrafluoroethylene (PTFE), ethylenetetrafluoroethylene (ETFE), perfluoroethylenepropylene (FEP), perfluoroalkoxy (PFA), etc., and also copolymers of these. Preferably, however, silicone or a silicone-containing material (copolymer) is used for the base material.

In a preferred refinement, the solid particles are introduced into the surface of the intermediate product mechanically. In this case, in general, a mechanical force is exerted upon the particles. In the simplest instance, this may be the weight. Alternatively or as a backup to a mechanical application, there is also the possibility of electrostatic application of the solid particles. In this case, electro(static) forces are utilized instead of mechanical forces. The loosely present solid particles are in this case, in particular, charged electrostatically before application.

Preferably, for mechanical introduction, in the second step, the intermediate product is led through a reservoir having solid particles contained therein. Since the intermediate product usually has high adhesiveness because of its at least partially non-cross-linked state, the solid particles are automatically caught on the surface.

In order to assist this adhesion of the solid particles and in order to achieve as homogeneous a degree of coverage as possible, the reservoir is preferably exposed to vibration, so that the solid particles are virtually pressed mechanically into the surface. The reservoir is therefore designed as a vibrating container. In principle, the element itself could also be moved back and forth mechanically.

In an expedient development, the reservoir is designed in the manner of a hopper through which the intermediate product is led. This also makes it possible, in particular, for the intermediate product, formed particularly as a string, to be led vertically through the reservoir in a continuous process. Alternative forms of the reservoir are likewise possible.

Alternatively to this, the intermediate product is led through a cyclone container in which an airstream or a vortex as a carrier stream is formed for the solid particles, so that these are swirled around and are therefore caught on the outer surface of the intermediate product.

The intermediate product itself is expediently formed as a result of an extrusion process, the solid particles preferably being introduced immediately thereafter in a continuous process. For this purpose, in particular, the intermediate product formed as an endless string is led through the reservoir.

In a preferred development, excess solid particles are removed again in a cleaning stage. This takes place, in particular, after the third step of cross-linking, so that all the solid particles not incorporated into the surface are therefore removed again. This takes place preferably by means of a washing process. For this purpose, the element is expediently led through a cleaning bath which, for example, is additionally acted upon ultrasonically.

The solid particles introduced into the surface are expediently laminated silicates (mica particles), micro glass balls, metal soaps or talc particles. Investigations have shown that the desired effect of a reduction in friction is especially marked particularly in the case of mica particles. Talc particles have also turned out to be suitable.

Investigations have shown, furthermore, that the size of the solid particles has a decisive influence upon the desired friction-reducing property. The solid particles preferably have a size which corresponds to a mesh size in the region of 320+/−40. Mesh is in this case the mesh width of a screen for separating the desired particles. The solid particles therefore preferably have generally a maximum particle size preferably in the range of 35 µm to 55 µm.

With a view to an especially efficient and economical production method, the article, particularly the cable, is produced in a continuous fully automatic process, the following steps being carried out directly in succession: first, the intermediate product is generated as a continuous string preferably in an extrusion process, and solid particles are subsequently introduced into the surface of the extruded string before the base material is then cross-linked. Thereafter, the product thus obtained is cleaned of excess solid particles, and finally the product obtained is typically wound, for example, on a drum.

The article is preferably in general an electrical cable designed as a sheathed line, with at least one line conductor which is surrounded by an outer sheath made from the silicone-like base material. The cable is, in particular, a data or signal cable in which a plurality of insulated line conductors are surrounded by a common outer sheath. The line conductors typically have an electrical conductor which is itself surrounded by insulation. The electrical conductor may be a solid wire or preferably an ultrafine or fine wire strand. The entire cable has, for example, a diameter in the range of about 1 mm-5 mm, the sheath thickness of the silicone outer sheath, lying, for example, in the range of 0.5 mm to 3 mm.

With the above and other objects in view there is also provided, in accordance with the invention, an article, comprising:

an outside surface formed of a silicone-type base material;

solid particles embedded in the surface of the base material for reducing a coefficient of friction of the surface;

the solid particles being mica particles pressed into the surface and distributed over the surface so that merely a dot-shaped contact zone is formed in each case, and at least some of the solid particles projecting out of the surface in the manner of scales.

This element is characterized in that solid particles are embedded only in the surface of the base material. The solid particles are therefore present only in a near-surface region, the volume of the base material itself consequently being free of solid particles. The depth of penetration of the particles into the surface therefore preferably corresponds to no more than the particle size.

Furthermore, there is preferably provision whereby at least some of the solid particles project out of the surface in the manner of scales. The solid particles in this case also preferably have no preferential orientation, but instead are embedded haphazardously or randomly into the surface. The solid particles are, in particular, flaky elements, in particular mica particles, and have a size preferably in the range of 35 µm-55 µm (measured in the direction of the greatest extent).

Other features which are considered as characteristic for the invention are set forth in the appended claims.

Although the invention is illustrated and described herein as embodied in a method for producing an element, particularly a cable, from a silicone-like base material, comprising introduction of solid material particles into the surface of an intermediate product, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1A:
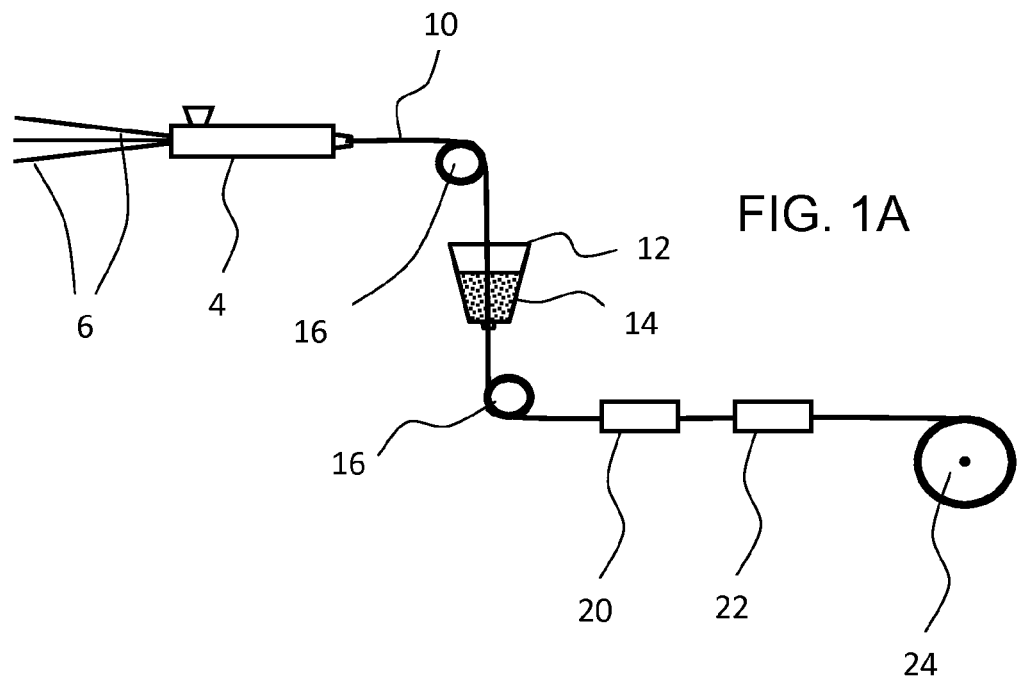
FIG. 1A-C show diagrams to illustrate the production method for producing a cable with a silicone outer sheath having solid particles introduced therein.
Figure 1B:
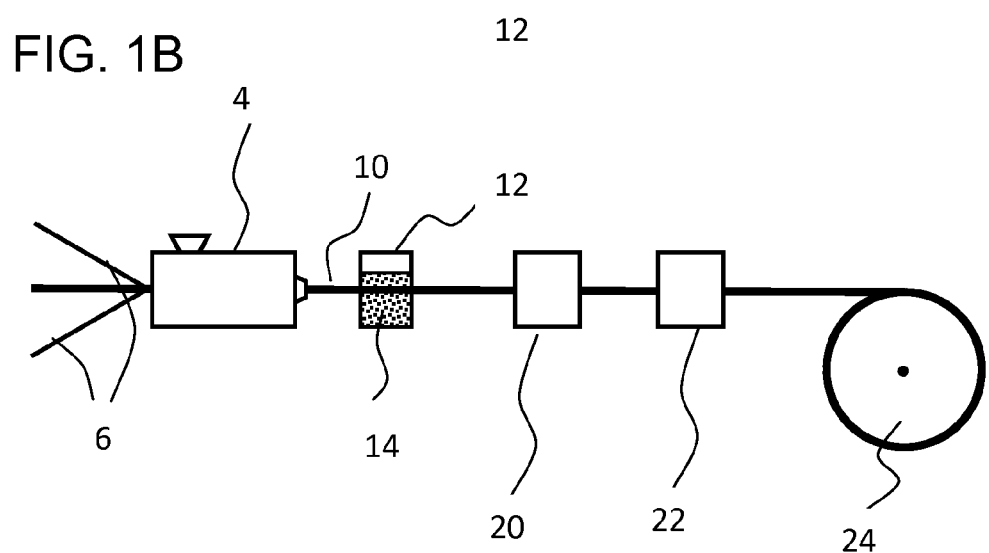
Figure 1C:
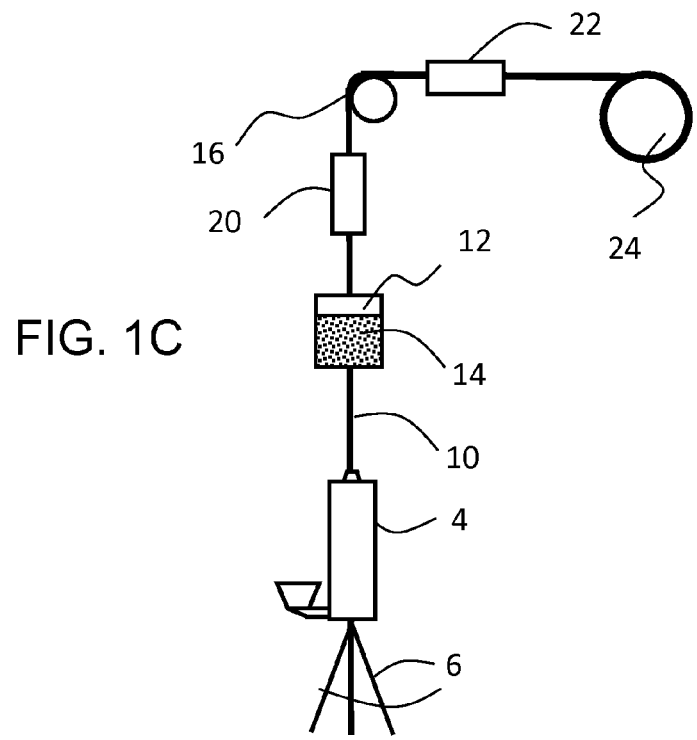

Referring now to the figures of the drawing in detail and first, particularly, to FIGS. 1A, 1B, and 1C, to produce a cable 2 which is first in the form of continuous stock, various installations and components may be employed. For example, three variants in each case modified in relation to one another are illustrated in the mentioned FIGS. 1A to 1C.

In all variants, a plurality of line conductors 6 are fed to an extruder 4 and within the framework of an extrusion process are surrounded with an outer sheath 8 made from a silicone-type base material. The outer sheath in this case surrounds the line conductors 8 directly. It therefore rests directly against the line conductors 6. In addition to the line conductors 6, if required, filler or hose elements or else strain relief threads may also be incorporated.

The base material used in the context is a silicone which, when it leaves the extruder 4, is still in an at least partially non-cross-linked state. An intermediate product 10 therefore emerges from the extruder 4. This intermediate product is subsequently guided in a continuous process through a reservoir 12 which is filled with solid particles 14, in particular mica particles, present as loose bulk material, or into which at least the solid particles are introduced.

In the design variant according to FIG. 1A, the reservoir 12 is preferably a vibrating hopper which can be set in vibration. The string-shaped intermediate product 10 runs through the reservoir 12 preferably in the vertical direction, selectively from the top downward (FIG. 1A) or from the bottom upward (FIG. 1C). Alternatively, a horizontal leadthrough through the reservoir is provided (FIG. 1B). The reservoir in FIG. 1B is in this case preferably designed in the manner of a cyclone container in which an airstream is generated, so that the solid particles 14 preferably stored in the reservoir 12 are swirled around.

Finally, in a non-illustrated further alternative, the solid particles 14 are applied with electrostatic backup. For this purpose, the solid particles 14 are first charged electrostatically and are subsequently brought into contact with the intermediate product 10. This preferably takes place, in turn, with the aid of a container 12, for example similar to that illustrated in FIG. 1B, in that the solid particles 14 are led through an electrostatic charging module and are subsequently applied to the intermediate product 10 from above in the manner of a trickling installation. If required, in this case, there may be backup by an airstream for the generation of turbulence.

After the solid particles 14 have been applied to the surface 18 (cf. FIG. 2), the intermediate product 10 is led through a cross-linking station 20 in order to cross-link, or completely cross-link the base material. Cross-linking takes place, for example, by thermal treatment or else by UV treatment etc. The intermediate product 10 may in each case be deflected via deflecting rollers 16. These are preferably arranged downstream of the cross-linking station 20, as illustrated in FIG. 1C. In the embodiment according to FIG. 1B, the deflecting rollers 16 are dispensed with entirely.

Finally, after the cross-linking station 20, the cable 2 also runs through a cleaning stage 22. In the exemplary embodiment, this is a cleaning container which is filled with a washing liquid. A drying stage may also be connected thereafter, before the finished cable 2 is then wound on a drum 24.

Figure 2:
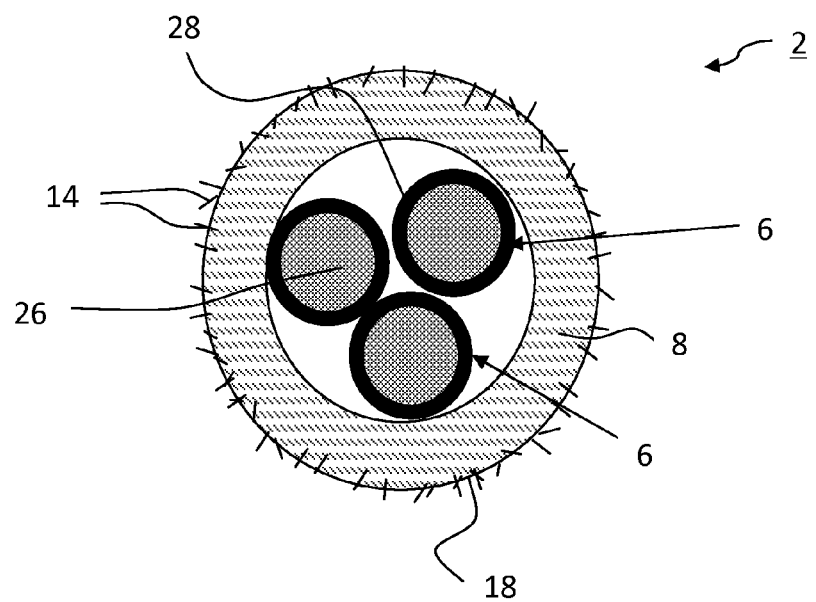
FIG. 2 shows a greatly simplified cross-section through a cable produced accordingly.

A cable 2 produced in this way is illustrated, for example, in FIG. 2. It may be gathered from this that the individual solid particles 14 are embedded, distributed homogeneously, into the surface 18 of the outer sheath 8, without penetrating into the inner volume. The surface 18 is in this case, in general, an outer surface, which may therefore come into contact with external objects. The individual line conductors 6 have in each case a central conductor 26 which is surrounded by conductor insulation 28. The group of line conductors 6 is surrounded directly by the outer sheath 8.

Still with reference to FIG. 2, the individual solid particles project somewhat out of the surface 18 in the manner of scales. They are formed, in particular, as flaky solid particles. The solid particles 14 are embedded solely in the surface 18 and penetrate into the surface 18 at most to about their particle size.

Figure 3:
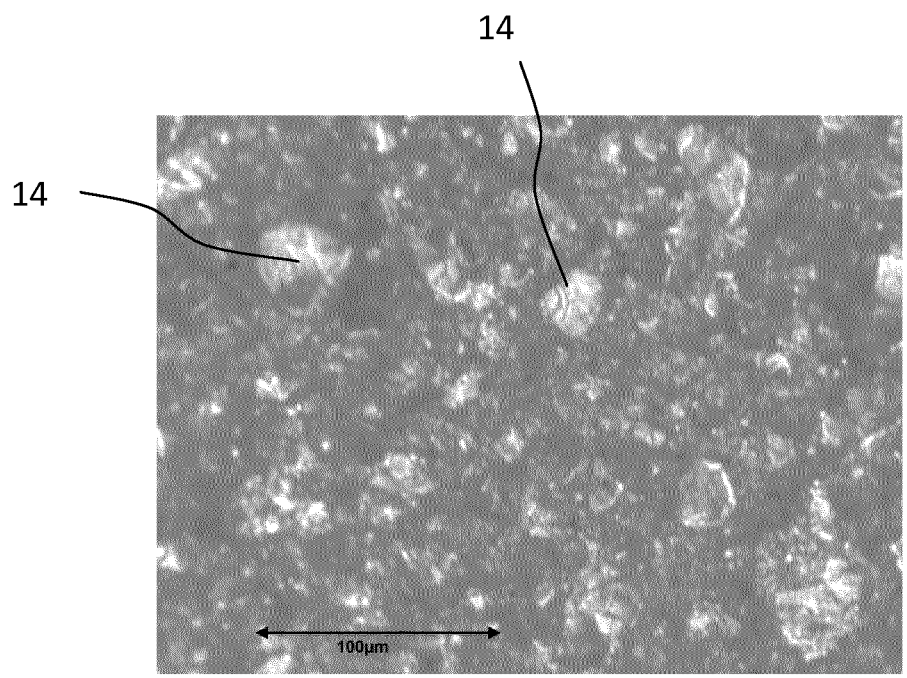
FIG. 3 shows a microscopic photograph (micrograph) of the surface of a cable produced in this way.

Finally, FIG. 3 also shows a microscopic magnification of a surface produced in this way, in which the individual solid particles 14 can be recognized from the bright regions. By contrast, the dark regions show the matrix of silicone material in which the solid particles 14 are embedded. The largest solid particles 14 therefore have a size of no more than about 45 μm.

The method described here is not necessarily limited to the production of an electrical cable having a silicone cable sheath. In principle, the fundamental idea, to be precise that of introducing solid particles into the surface of a silicone element in order to improve the feel and, in particular, to reduce the coefficient of friction, can also be applied to other products which have a silicone-like base material on their surface. By means of the method described here, a silicone product with a pleasant feel and with a low coefficient of friction is provided in a simple way in terms of the process employed. The use of mica particles with a grain size in the range of 35 μm to 45 μm has turned out to be especially advantageous in this case. Silicone products of this type are suitable particularly for medical applications. Use in cables particularly for the medical sector is especially advantageous, since, as a result, handling is improved and disruptive adhesion to surfaces or even to the skin is avoided.

The following is a summary list of reference numerals and the corresponding structure used in the above description of the invention:

2 cable
4 extruder
6 line conductor
8 outer sheath
10 intermediate product
12 reservoir
14 solid particles
16 deflecting roller
18 surface 20 cross-linking station
22 cleaning stage
24 drum
26 conductor
28 conductor insulation.

The invention claimed is:

1. A method of producing an article with an exterior surface of a silicone-type material, the method comprising:
   in a first step, fashioning an at least partially non-cross-linked base material into an intermediate product;
   subsequently, in a second step, introducing solid mica particles into the surface by guiding the at least partially non-cross-linked intermediate product through a reservoir containing the solid mica particles therein, and exposing the reservoir to vibration or generating in the reservoir a vortex or an airstream to thereby mechanically press the solid mica particles into the surface and to cause the particles to be distributed over the surface, with a dot-shaped contact zone formed in each case, and wherein at least some of the solid mica particles project out of the surface as scales; and
   subsequently, in a third step, cross-linking the at least partially non-cross-linked base material.

2. The method according to claim 1, wherein the reservoir is a vibrating hopper and the intermediate product is guided through the hopper.

3. The method according to claim 1, which comprises producing the intermediate product in an extrusion process and introducing the solid particles immediately after the extrusion.

4. The method according to claim 1, which comprises, following the third step of cross-linking, removing excess solid mica particles.

5. The method according to claim 1, which comprises providing the solid mica particles with a maximum particle size of 35 µm-55 µm.

6. The method according to claim 1, which comprises carrying out the following steps directly in succession in a continuous process:
   producing the intermediate product as a continuous string in an extrusion process;
   introducing the solid particles into the surface of the intermediate product;
   cross-linking the silicone-type base material and, if required, cleaning off excess solid particles; and
   winding-up of the string.

7. The method according to claim 1, which comprises producing a cable.

8. The method according to claim 7, wherein the article is an electrical cable formed as a sheathed line, having at least one line conductor which is surrounded by an outer sheath made from the silicone-type base material.

9. An article, comprising:
   an outside surface formed of a silicone-type base material;
   solid particles embedded in said surface of said base material for reducing a coefficient of friction of said surface;
   said solid particles being mica particles pressed into said surface and distributed over said surface so that merely a dot-shaped contact zone is formed in each case, and at least some of said solid particles projecting out of said surface in the manner of scales.

10. The article according to claim 9, configured as a cable.

11. The article according to claim 9, wherein said solid particles have a maximum particle size of between 35 µm and 55 µm.

12. The article according to claim 11, wherein a depth of penetration of said solid particles into said surface is less than or equal to the particle size, and a remaining base material is free of solid particles.

13. The article according to claim 9, wherein a depth of penetration of said solid particles into said surface is less than or equal to a particle size thereof, and a remaining base material is free of solid particles.

14. The article according to claim 9, wherein said solid particles are embedded in said surface without any preferential orientation.

* * * * *